(12) United States Patent
Wiltberger et al.

(10) Patent No.: US 7,452,080 B2
(45) Date of Patent: Nov. 18, 2008

(54) SCANNING OPHTHALMIC FIXATION METHOD AND APPARATUS

(75) Inventors: Michael W. Wiltberger, Santa Clara, CA (US); Dan E. Andersen, Menlo Park, CA (US)

(73) Assignee: Optimedica Corporation, Santa Clara, CA (US)

( * ) Notice: Subject to any disclaimer, the term of this patent is extended or adjusted under 35 U.S.C. 154(b) by 111 days.

(21) Appl. No.: 11/149,723

(22) Filed: Jun. 9, 2005

(65) Prior Publication Data

US 2005/0286019 A1     Dec. 29, 2005

Related U.S. Application Data (60) Provisional application No. 60/578,953, filed on Jun. 10, 2004.

(51) Int. Cl.
*A61B 3/10* (2006.01)
(52) U.S. Cl. .................... 351/211; 351/221; 351/246
(58) Field of Classification Search ............... 351/211, 351/221, 246
See application file for complete search history.

(56) References Cited

U.S. PATENT DOCUMENTS

| | | | |
|---|---|---|---|
| 3,703,176 A | 11/1972 | Vassiliadis et al. | |
| 3,883,235 A | 5/1975 | Lynn et al. | |
| 3,982,828 A | 9/1976 | Woolf | |
| 4,255,022 A | 3/1981 | Kuether et al. | |
| 4,431,278 A * | 2/1984 | Nohda .................... | 351/211 |
| 4,536,065 A | 8/1985 | Sheingorn | |
| 4,620,318 A * | 10/1986 | Hill .................... | 382/117 |
| 4,685,784 A | 8/1987 | Kirchhuebel | |
| 4,884,884 A | 12/1989 | Reis | |
| 4,917,486 A | 4/1990 | Raven et al. | |
| 4,952,050 A | 8/1990 | Aizu | |
| 5,293,532 A | 3/1994 | Marshall | |
| 5,391,165 A | 2/1995 | Fountain et al. | |
| 5,425,729 A | 6/1995 | Ishida et al. | |
| 5,480,396 A | 1/1996 | Simon et al. | |
| 5,514,127 A | 5/1996 | Shanks | |
| 5,543,866 A | 8/1996 | Van De Velde | |

(Continued)

FOREIGN PATENT DOCUMENTS

WO    WO 95/27453    10/1995

(Continued)

OTHER PUBLICATIONS

Barrett, Steven et al., "Computer-Aided Retinal Photocoagulation System", *Journal of Biomedical Optics* 1(1), Jan. 1996, pp. 83-91.

(Continued)

*Primary Examiner*—Jordan M. Schwartz
(74) *Attorney, Agent, or Firm*—DLA Piper LLP (US)

(57) ABSTRACT

An apparatus and method for treating and/or diagnosing a patient's eye. A light source produces fixation light and procedure (treatment and/or diagnosis) light. A scanning device deflects the fixation light to produce a fixation pattern of the fixation light on the eye, and deflects the procedure light to produce a procedure pattern of the procedure light on the eye. A controller controls the scanning device such that the fixation and procedure patterns move relative to each other, and/or the fixation pattern dynamically changes.

31 Claims, 10 Drawing Sheets

U.S. PATENT DOCUMENTS

| | | | |
|---|---|---|---|
| 5,568,208 | A | 10/1996 | Van De Velde |
| 5,618,285 | A | 4/1997 | Zair |
| 5,688,264 | A | 11/1997 | Ren et al. |
| 5,743,902 | A | 4/1998 | Trost |
| 5,776,068 | A | 7/1998 | Silverman et al. |
| 5,828,439 | A * | 10/1998 | Ueno .................. 351/205 |
| 5,892,569 | A | 4/1999 | Van De Velde |
| 5,921,981 | A | 7/1999 | Baymanyar et al. |
| 5,943,117 | A | 8/1999 | Van De Velde |
| 5,957,915 | A | 9/1999 | Trost |
| 5,971,978 | A | 10/1999 | Mukai |
| 5,980,513 | A | 11/1999 | Frey et al. |
| 6,011,563 | A | 1/2000 | Fournier |
| 6,066,128 | A | 5/2000 | Bahmanyar et al. |
| 6,096,028 | A | 8/2000 | Bahmanyar et al. |
| 6,149,644 | A | 11/2000 | Xie |
| 6,186,628 | B1 | 2/2001 | Van De Velde |
| 6,238,385 | B1 | 5/2001 | Harino et al. |
| 6,267,756 | B1 | 7/2001 | Feuerstein et al. |
| 6,328,733 | B1 | 12/2001 | Trost |
| 6,347,244 | B1 | 2/2002 | Dubnack |
| 6,494,878 | B1 | 12/2002 | Pawlowski et al. |
| 6,607,527 | B1 | 8/2003 | Ruiz et al. |
| 6,705,726 | B2 | 3/2004 | Tanassi et al. |
| 6,789,900 | B2 | 9/2004 | Van De Velde |
| 6,802,837 | B2 | 10/2004 | Donitzky et al. |
| 7,146,983 | B1 | 12/2006 | Hohla |
| 2003/0009155 | A1 | 1/2003 | Pawlowski |
| 2006/0100677 | A1 * | 5/2006 | Blumenkranz et al. ........ 607/89 |

FOREIGN PATENT DOCUMENTS

| | | |
|---|---|---|
| WO | WO 00/21475 | 4/2000 |

OTHER PUBLICATIONS

Van de Velde, "Role Of The Scanning Laser Ophthalmoscope In Photodynamic Therapy Of Macular Disease", *Ophthalmic Technologies X, Proceedings of SPIE*, vol. 3908 (2000), pp. 190-201.

Barrett, Steven F. et al., "Digital Imaging-Based Retinal Photocoagulation System", *SPIE*, vol. 2971, pp. 118-128.

Wright, Cameron et al., "Initial In Vivo Results Of A Hybrid Retinal Photocoagulation System", *Journal Of Biomedical Optics*, vol. 5, No. 1, Jan. 2000, pp. 56-61.

Naess et al., "Computer-Assisted Laser Photocoagulation Of The Retina-a Hybrid Tracking Approach", Journal of Biomedical Optics, Apr. 2002, vol. 7, No. 2, pp. 179-189.

Markow, M.S. et al., "An Automated Laser System For Eye Surgery", *IEEE Engineering In Medicine & Biology Magazine*, vol. 8, Dec. 1989, pp. 24-29.

Wright, Cameron et al., "Hybrid Approach To Retinal Tracking And Laser Amining For Photocoagulation", *Journal of Biomedical Optics* 2(2), Apr. 1997, pp. 195-203.

\* cited by examiner

SCANNING OPHTHALMIC FIXATION METHOD AND APPARATUS

This application claims the benefit of U.S. Provisional Application No. 60/578,953, filed Jun. 10, 2004.

FIELD OF THE INVENTION

The present invention pertains generally to instruments and methods for fixating a patient's eye for ophthalmic examination and/or treatment, and specifically for doing so with a scanning light source.

BACKGROUND OF THE INVENTION

It is generally known that there is a variety of ways in which to ophthalmoscopically examine the eye, and that they all require at least some degree of patient fixation. Fixation includes the act of attracting and keeping the patient's gaze in a nominally fixed direction in order to keep the eye steady. To date, however, approaches to patient fixation devices have been largely limited to static, discrete points of light (e.g. images on a fixed screen or physical objects simply placed in the patient's field of view).

In U.S. Pat. No. 3,883,235, Lynn, et al disclose the use of a monitor to track the patient's gaze, and allow for the adjustment of an image on a screen to compensate for the patient's lack of fixation during a visual field examination. This solution, however, simply accommodates the problem of a patient's inherent fixation difficulties, rather than solving it.

In U.S. Pat. No. 4,536,065 Sheingorn discloses the use of a fixation device for the eye testing of children that uses several movable and light-emitting toys which are housed in display panel and remotely controlled by foot of an optician.

Marshall (U.S. Pat. No. 5,293,532) and Kirchhuebel (U.S. Pat. No. 4,685,784) disclose the use of a fixed array of light emitting diodes (LEDs) in order to fixate the patient's gaze. Marshall makes use of LEDs embedded in a patch which is worn over one eye while the other is being observed. While this allows the image of the LEDs to appear at infinity, and thereby relax the eye muscles, it is nevertheless awkward and patients may find it uncomfortable. Kirchhuebel positions the LEDs further away from the eye such that they are only simultaneously visible when the patient's head is in a precise location.

In U.S. Pat. No. 6,705,726, Tanassi discloses the use of a multipurpose ophthalmic diagnostic device containing a liquid crystal display (LCD) for patient fixation. This device provides for the projection of various types of patterns and stimuli via an optical system onto the retina.

Accordingly, it is desirable to provide a system and method for patient eye fixation that is inherently flexible, dynamic, compact, and uncomplicated. This is especially true when used to image tissue with Optical Coherence Tomography (OCT), or Scanning Laser Ophthalmoscopy (SLO) systems, or when used to apply burns to the retina with a therapeutic device such as a laser photocoagulator, especially a scanning laser photocoagulator.

SUMMARY OF THE INVENTION

The present invention solves the aforementioned problems by providing an optical scanning system for treating and/or diagnosing a patient's eye. The system includes a light source for producing fixation light and procedure light, a scanning device for deflecting the fixation light to produce a fixation pattern of the fixation light on the eye, and for deflecting the procedure light to produce a procedure pattern of the procedure light on the eye, and a controller for controlling the scanning device such that at least one of the fixation and procedure patterns is moved relative to the other of the fixation and procedure patterns.

In another aspect of the present invention, the optical scanning system for treating and/or diagnosing a patient's eye includes a light source for producing fixation light and procedure light, a scanning device for deflecting the fixation light to produce a fixation pattern of the fixation light on the eye, and for deflecting the procedure light to produce a procedure pattern of the procedure light on the eye, and a controller for controlling the scanning device such that the fixation pattern dynamically changes.

In still one more aspect of the present invention, the optical scanning system for treating and/or diagnosing a patient's eye includes a light source for producing fixation light and procedure light, a scanning device for deflecting the fixation light to produce a fixation pattern of the fixation light on the eye and for deflecting the procedure light to produce a procedure pattern of the procedure light on the eye, and a controller for controlling the scanning device such that the fixation pattern and the procedure pattern do not overlap each other on the eye.

In yet another aspect of the present invention, a method of treating and/or diagnosing a patient's eye includes generating fixation light, generating procedure light, deflecting the fixation light to produce a fixation pattern of the fixation light on the eye, deflecting the procedure light to produce a procedure pattern of the procedure light on the eye, and moving at least one of the fixation and procedure patterns relative to the other of the fixation and procedure patterns.

In yet one more aspect of the present invention, a method of treating and/or diagnosing a patient's eye includes generating fixation light, generating procedure light, deflecting the fixation light to produce a fixation pattern of the fixation light on the eye, deflecting the procedure light to produce a procedure pattern of the procedure light on the eye, and dynamically changing the fixation pattern on the eye.

In yet one additional aspect of the present invention, a method of treating and/or diagnosing a patient's eye includes generating fixation light, generating procedure light, deflecting the fixation light to produce a fixation pattern of the fixation light on the eye, deflecting the procedure light to produce a procedure pattern of the procedure light on the eye, wherein the deflectings are performed such that the fixation pattern and the procedure pattern do not overlap each other on the eye.

Other objects and features of the present invention will become apparent by a review of the specification, claims and appended figures.

DETAILED DESCRIPTION OF THE PREFERRED EMBODIMENTS

The present invention is an apparatus and method for producing ophthalmic patient fixation by illuminating the patient's retina using an optical scanning system with a primary pattern of light P (for patient eye fixation) and a secondary pattern of light S (for patient eye treatment and/or diagnosis). Patterns P and S may each be comprised of a single discrete spot, multiple discrete spots, a continuous scan, a discontinuous scan (i.e. continuously scanned segments), or any combination thereof. Furthermore, an image (as opposed to simple illumination) may be produced on a patient's retina as well.

The fundamental purpose of pattern P is to provide a moving or dynamically changing fixation target on which the patient can lock his/her eyes. The output geometry of the light source producing pattern P need not be round. In order to obtain and keep a patient's attention (fixation), pattern P is preferably dynamic. Therefore, the actual pattern P, or any of its elements, can change, move and/or be perceived as blinking in order to further enhance its effects. Since it is tedious and tiresome to stare at a static target in a fixed direction for too long a period of time, it is desirable that pattern P may be easily repositioned, its character altered, or both to keep the patient fixated during a eye treatment and/or diagnostic procedure.

Once aligned, and the patient properly fixated, an ophthalmic procedure may be performed in which treatment and/or diagnostic light of pattern S is directed into the eye. Hereinafter, treatment and/or diagnostic light is referred to as procedure light. Such a procedure can be diagnostic such as Scanning Laser Ophthalmoscopy (SLO) and Optical Coherence Tomography (OCT), and/or can be therapeutic such as photodisruption (PD), photocoagulation (PC), Laser Iridectomy (LI), Laser Trabeculoplasty (LT), Photodynamic Therapy (PDT), Selective Laser Trabeculoplasty (SLT), and Selective RPE Therapy (SRT). These procedures are well known in the art, and therefore are not described in further detail. The final relationship between primary pattern P and any secondary pattern(s) S associated with an ophthalmic procedure is completely arbitrary, and each pattern may be positioned independently of the other(s). In this way, pattern P may be moved relative to pattern S, and vice-versa, as dictated by the particular immediate clinical need. As an example, pattern P may be used to fixate the patient's eye, having them look away from the optical axis of the physician's visualization and procedure light delivery system, thereby giving direct optical access to the retinal periphery, and pattern S may be an array of laser spots, such as those of a Pan Retinal Photocoagulation (PRP) procedure.

It is understood that patterns are preferably created using a scanner, and that a scanner minimally includes a light source, and a means with which to spatially deviate the optical output of the light source.

Figure 1:
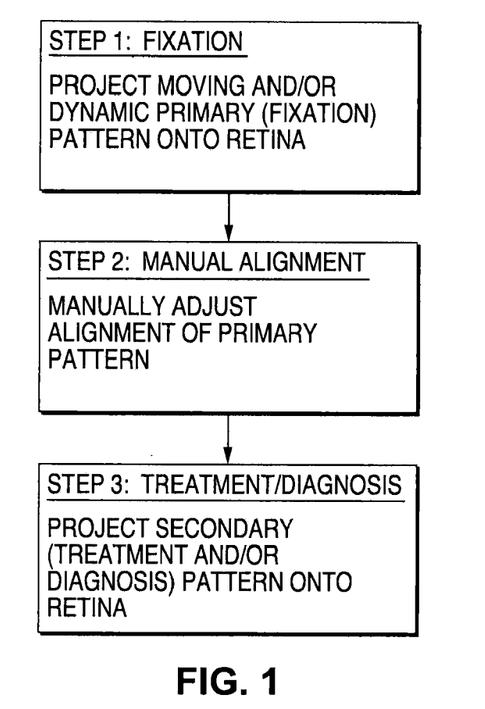
FIG. 1 is a flow diagram of a method of the present invention.

FIG. 1 is a flow diagram of a method of the present invention. First, in Step 1, the patient's eye is fixated by projecting a moving (relative to procedure pattern S) and/or dynamically changing primary (fixation light) pattern P of light onto the retina (i.e. which includes moving pattern S relative to a stationary pattern P). Second, in Step 2, the system operator may manually align pattern P to achieve the desired eye positioning and fixation. This second step is optional. The primary pattern P attracts the patient's attention and allows them to easily fixate, thus positioning the eye to allow an ophthalmic procedure to be performed. Third, in Step 3, a procedure is conducted by projecting a secondary (procedure light) pattern S of light onto the retina. This third step may include projecting an aiming beam of visible light before or during the projection of procedure pattern S to ensure it is properly positioned. The patient may be made to look in a preferred direction so that patterns P and S need not necessarily overlap, although they certainly could.

Figure 2:
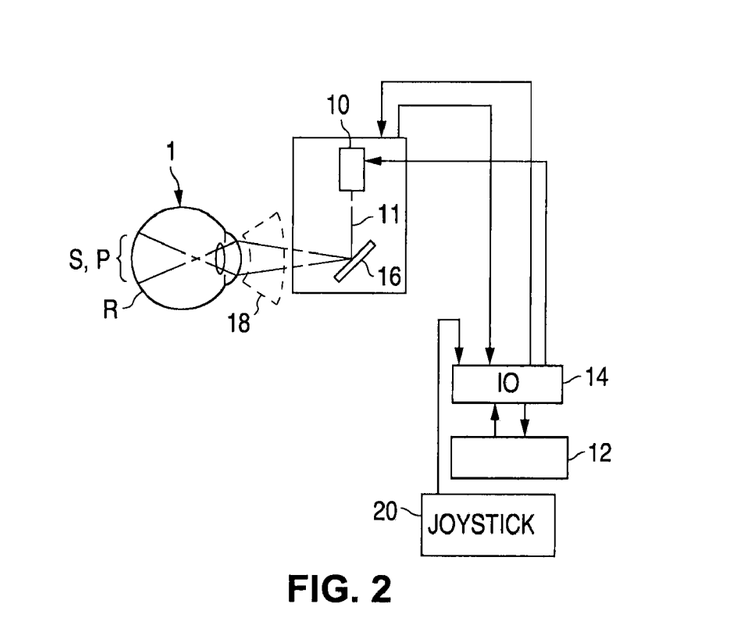
FIG. 2 is a schematic view of the present invention.

FIG. 2 shows a schematic diagram of a system suitable for performing the method of FIG. 1 on a patient's eye 1. Pattern P is created using light source 10, which may be controlled by control electronics 12, via an input and output device 14, to create optical beam 11. Control electronics 12 may be a computer, microcontroller, etc. In this embodiment, scanning may be achieved by using a moveable mirror 16 which also may be controlled by control electronics 12, via input and output device 14. Mirror 16 may be tilted to deviate the optical beam 11, whose centerlines are shown as dashed lines in the figures, and direct beam 11 towards the retina R of the patient's eye 1. The beam 11 will be nominally focused by the eye itself and finally perceived by the patient. The final image of pattern P is disposed at the patient's retina R. However, the use of an optional ophthalmic lens 18 dictates that the image of pattern P may be first made before retina R. Ophthalmic lens 18 may then serve to relay that image to retina R. The position and character of pattern P may be further controlled by use of an input device 20 such as a joystick, or any other appropriate user input device. The ultimate disposition of the optical output of light source 10 is essentially limited only by the optics of the system and any patient idiosyncrasies which might serve to perturb pattern P. Examples of such idiosyncrasies are cataracts, retinal inhomogeneities, and intraocular debris.

Light source 10 also produces the procedure light to form pattern S on the eye. Light source 10 can include one or more distinct light sources including diode-pumped solid state lasers, gaseous lasers, semiconductor lasers, light emitting diodes, flash lamps, etc. It is envisioned that the wavelength of light used to produce pattern P is different than that for pattern S. If the apparatus uses a single scanning apparatus used by both the fixation light and the procedure light, then these two light beams can be temporally interleaved either by gated the light beams on and off by commands from control electronics 12 via input and output device 14, or externally to the light source 10. Light source can be gated to produce discrete spots, or simply run continuously (cw) to create continuous scans as a means to produce patterns P and S. Control electronics 12 likewise controls the position of mirror 16 and therefore, ultimately, the patterns P and S. In this way, pattern P, or any of its elements, may be made to be perceived by the patient as blinking. Furthermore, the perception of both discrete spots and blinking may be accomplished by simply scanning quickly between elements of pattern P so as to limit the amount of light registered by the patient in those intermediate spaces. The inherent flexibility of scanned light sources thus enables many desired clinical possibilities. A device such as this may be mounted directly onto, among other things, an ophthalmic visualization tool such as a slit lamp biomicroscope, fundus camera, SLO, or OCT system.

An optical scan to form patterns P and S can be created in a number of different ways, such as by moving light source 10 directly, moving mirror 16, using one or more rotating wedges, using a two-dimensional acousto-optic deflector, etc. Preferably, mirror 16 may be rotated as already described, or in the case of a mirror with surface curvature (optical power), it may also be translated to produce optical deviation. In the case where mirror 16 has optical power, compensating optical elements (not shown) may be required to produce an image, as opposed to a simple illumination.

Figure 3:
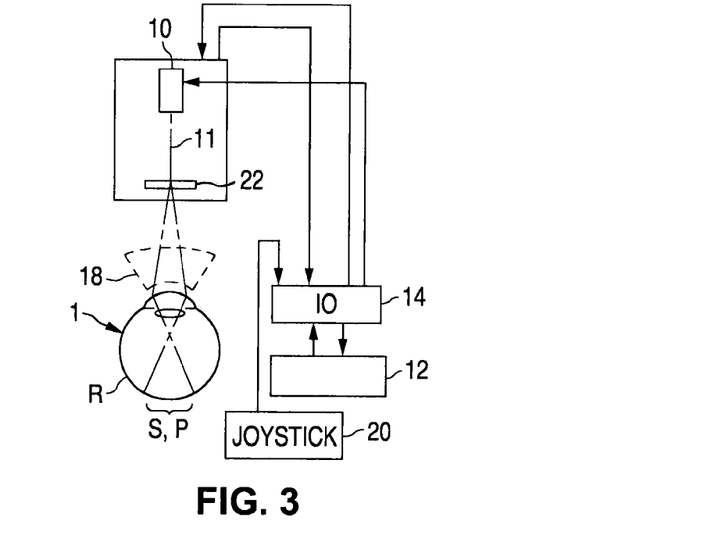
FIG. 3 is a schematic view of an alternate embodiment of the present invention.

FIG. 3 shows a schematic diagram of an alternate embodiment which is similar to that of the above discussion of FIG. 2, but with the mirror 16 being replaced by a moveable lens 22. Lens 22 may be either tilted or translated in order to produce a scan to form patterns P and S. A combination of scanning mirrors and lenses is also possible.

Figure 4A:
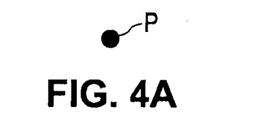
FIGS. 4A-4H show representative fixation targets that are comprised of discrete spots and/or continuous scans.
Figure 4B:
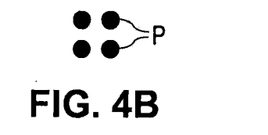
Figure 4C:
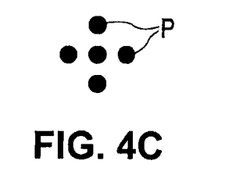
Figure 4D:
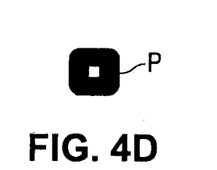
Figure 4E:
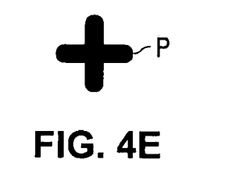
Figure 4F:
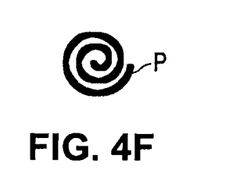
Figure 4G:
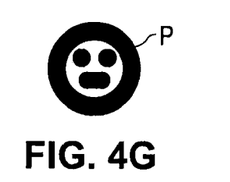
Figure 4H:
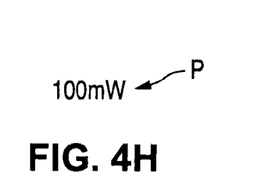

Primary pattern P can take one of many possible forms, as illustrated in FIGS. 4A-4H. For example, Pattern P may be a single discrete spot (FIG. 4A), multiple discrete spots (FIGS. 4B and 4C), a continuous scan (FIGS. 4D-4G), or any combination thereof (FIG. 4H). Although discrete spot(s) are shown as round, it is not a requirement that either the fundamental output geometry of light source 10, or the ultimate spot shape, be round. Creating a pattern accomplishes this same effect, especially when no intermediate spaces are left, such as may be done with FIGS. 4D & 4F. The image shown in FIG. 4H not only provides a fixation target for the patient, but also provides system information (e.g. power level, system status, pulse duration, etc.) viewable by the physician operating the system. In the case of FIG. 4H, the image illustrates the laser power level for the therapeutic procedure.

Figure 5:
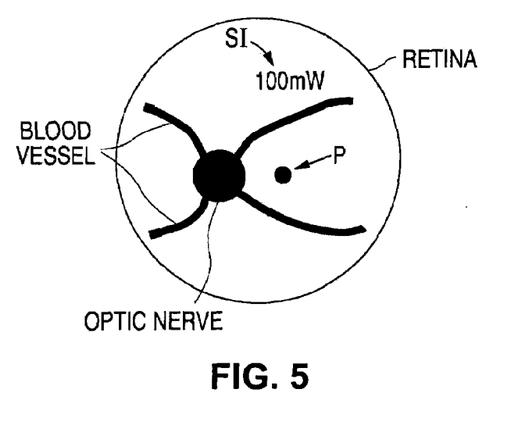
FIG. 5 illustrates the use of fixation targets such as that shown in FIG. 4H for the display of information to the physician.

Fixation and system information can also be projected onto the patient's eye separately. For example, fixation pattern P can be projected on one part of the eye for patient fixation, while system information may be projected on another part of the eye for physician use. Different light sources could be used to accomplish this (e.g. a bright green light that is highly visible could used to fixate the patient, while a less visible red light displays the information to the physician so as not to distract the patient). FIG. 5 illustrates the concept of combining patient fixation with system information display, where a fixation pattern P is projected onto the patient's fovea (highly visible to the patient), while a system information pattern SI is projected onto a periphery of the field of view of the patient's eye. The information may be shown continuously, or only briefly upon a change of system parameters.

Figure 6A:
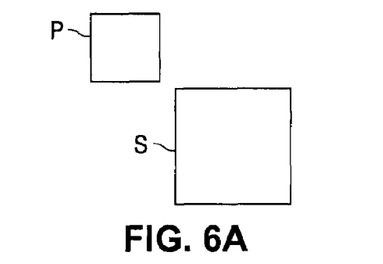
FIGS. 6A-6C illustrate the relative distinctions between the primary pattern, P, and the secondary pattern, S, where patterns S and P may each be individually comprised of a single discrete spot, multiple discrete spots, continuous scans, or any combination thereof.
Figure 6B:
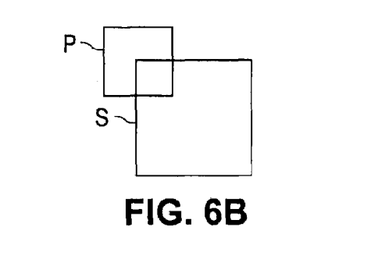
Figure 6C:
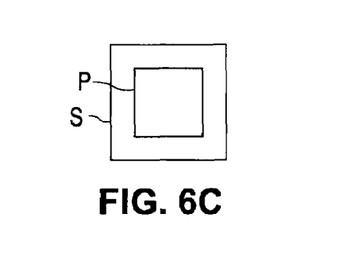

FIGS. 6A-6C show example relationships between primary pattern P for fixation, and secondary pattern S for treatment and/or diagnosis. The patterns can be completely separated (see FIG. 6A), partially overlap (see FIG. 6B) or one can completely overlap the other (see FIG. 6C). The tremendous advantage of the present invention however is that pattern P can be independently positioned relative to pattern S, and can be dynamically changed (blinking, change in size, color, and/or shape, etc.) relative to pattern S, for better quality and positioned eye fixation. For example, pattern P can be fixed while pattern S moves, and vice versa, as explained further below. In fact, even both patterns can move simultaneously (but not uniformly). Pattern P is shown in FIGS. 6A-6C as being smaller than pattern S, but need not be. Like pattern P, pattern S may be a single discrete spot, multiple discrete spots, a continuous scan, or any combination thereof, and should be dictated by specific clinical needs. Pattern S may be associated with a therapeutic ophthalmic procedure, such as PD, PC, LI, LT, PDT, SLT, SRT. These procedures may also be scanning procedures (such as SLO, OCT, PD, PC, LI, LT, SLT, and SRT), where pattern S is scanned into the eye.

Pattern P may be used to fixate the patient, having them look away at a fixed position away from the optical axis of the physician's visualization and procedure light delivery system and thereby gain direct optical access to the retinal periphery. At the same time, pattern S may be an array of laser spots as part of a PRP procedure, applied while the patient's eye is fixated. Alternately, pattern P can be moving during the administration of pattern S. As a first example, pattern P is moved to intentionally move the eye during treatment/diagnosis. In this way, pattern S may actually be kept stationary, and still ultimately be disposed onto relatively larger areas due to the relative motion between patterns S and P as the patient's eye follows pattern S. As a second example, small motion of pattern P is used to minimize actual eye movement while still capturing the patient's attention (which may be especially useful in situations such as pan retinal laser photocoagulation treatment where slight eye movement can be easily tolerated). In this second example, pattern P is slightly moved about a center position, which serves to attract the patient's attention and allow them to easily maintain fixation on pattern P (which may be especially useful during macular grid laser photocoagulation treatment, as unintended laser exposure to the central vision is to be absolutely avoided). Furthermore, pattern P may be spatially and/or temporally interleaved with pattern S to keep the patient fixated during the entire procedure.

Figure 7A:
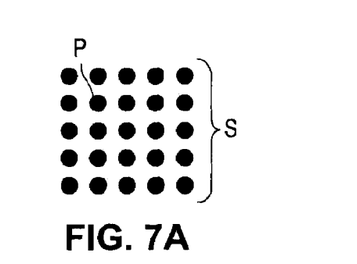
FIGS. 7A-7C illustrate relative distinctions between the primary pattern, P, and the secondary pattern, S, where pattern P is a single spot, and pattern S is comprised of an array of spots, such as might be used, for example, in conjunction with a scanned pulsed photocoagulator.
Figure 7B:
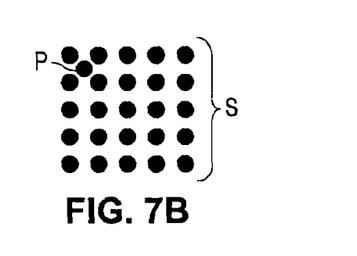
Figure 7C:
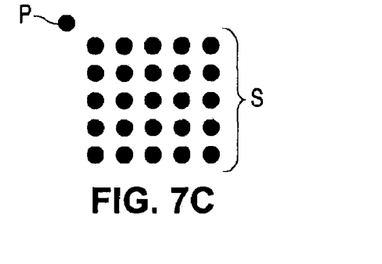

FIGS. 7A-7C show exemplary relationships between patterns S and P as might be specifically used in, for example, PD, PC, SRT, LI, LT, or SLT. Pattern P is shown as single round spot, but it need not be. Likewise, pattern S can be of any practical shape and size, but is simply represented here as a plurality of round spots in a rectangular configuration. Pattern S, or any of its elements need not be necessarily coincident with pattern P, or any of its elements. Their relationship can be dictated by clinical need. In the case where pattern S is a scanning procedure, pattern P may, but need not, be produced by the same scanning mechanism as that which creates pattern S. As illustrated, pattern P can be a single spot taking the place of a spot in an ordered pattern of spots in pattern S (FIG. 7A), disposed among an ordered pattern of spots in pattern S (FIG. 6B), or disposed outside of pattern S (FIG. 7C).

Figure 8A:
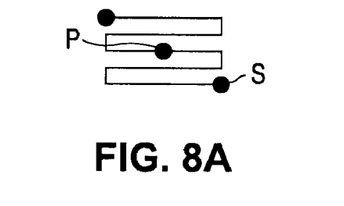
FIGS. 8A and 8B show exemplary relationships between patterns S and P as may be specifically used in conjunction with a constant wave light source.
Figure 8B:
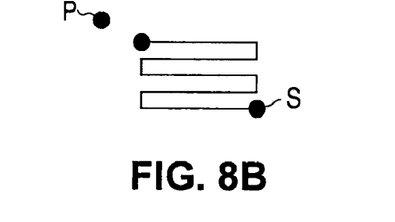

FIGS. 8A and 8B illustrate additional exemplary relationships between patterns S and P. Here, pattern P is a single spot, and pattern S is comprised of a continuous raster scan, such as might be used for example in conjunction with an imaging device such as an SLO or OCT system. Pattern P can overlap with a raster scanned pattern S (FIG. 8A) or not (FIG. 8B).

Figure 9:
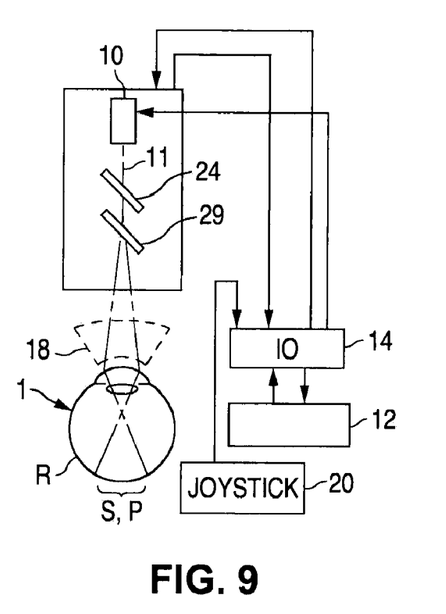
FIG. 9 is a schematic view of a second alternate embodiment of the present invention.

FIG. 9 shows a schematic diagram of a second embodiment of the present invention, which is similar to that discussed with respect to FIGS. 2 and 3, but with the addition of another scanning element. In this embodiment, scanning is achieved by using a pair of orthogonal optical elements 24 and 26, each able to move or deflect the optical beam 11 in one of two orthogonal directions. Optical elements 24/26 could be any combination of mirrors, lenses, diffractive elements etc. that can be used to move/deflect the beam 11. Optical elements 24/26 may be mounted upon, for example, galvanometers, solenoids, piezoelectric actuators, motors, etc. that move or tilt the optical elements 24/26, which in turns moves/deflects the beam 11. In this embodiment, beam 11 would include light for both S and P patterns, preferably temporally interleaved, so that a single scanning system (i.e. optical elements 24/26) can be used to generate both fixation and procedure patterns P and S.

Figure 10:
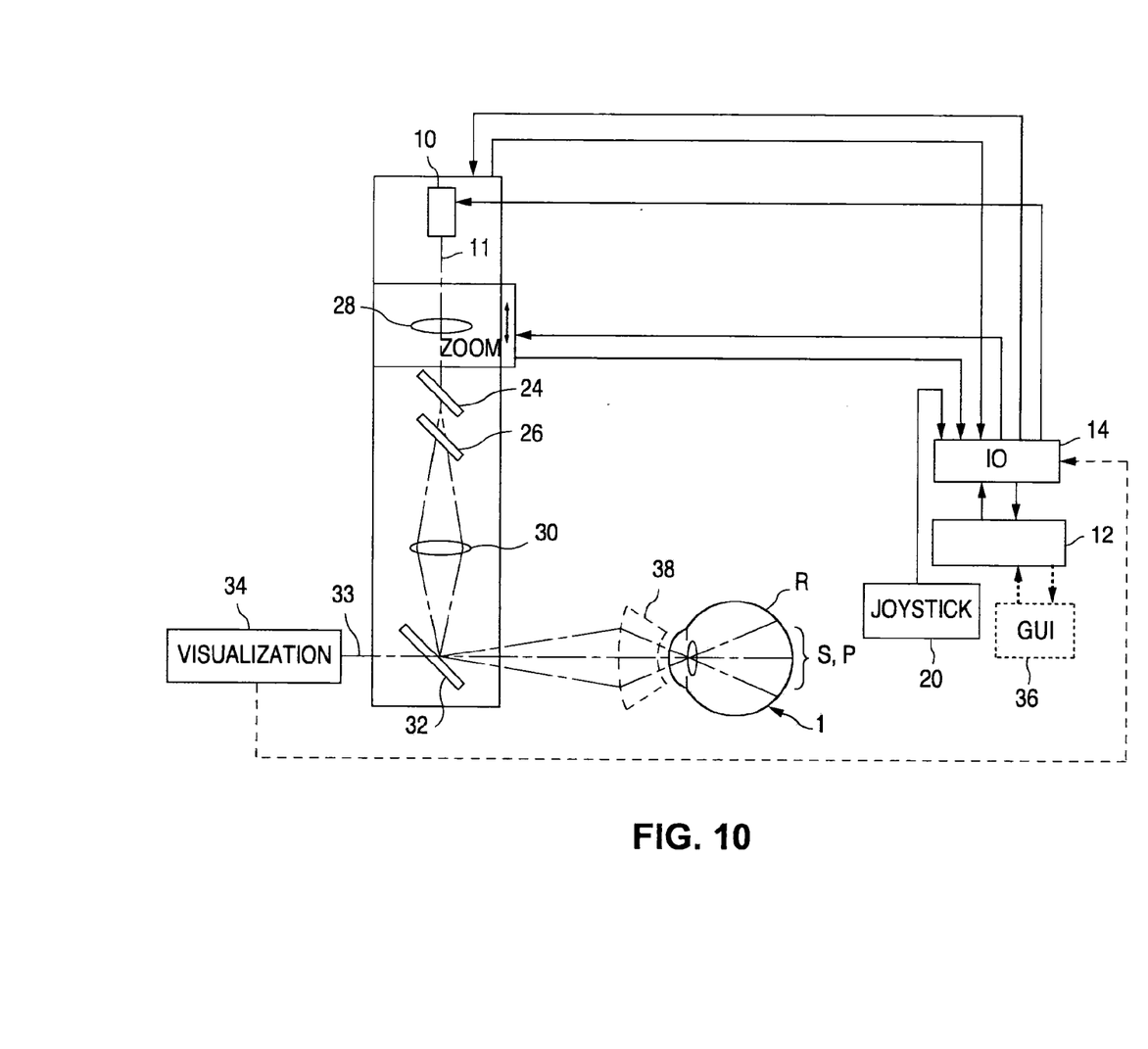
FIG. 10 is a schematic view of a third alternate embodiment of the present invention.

FIG. 10 shows a schematic diagram of a third alternate embodiment which is similar to that discussed above with respect to FIG. 9, but with the addition of lenses 28 and 30, and visualization 34. Lens 28 may be a single lens, or a compound lens, and can be configured as a zoom lens (e.g. a lens, or combination of lenses, moved manually or by motor/actuator along the axis of beam 11) for adjusting the intrinsic size of the beam that comprises patterns P and S. This is useful for easily adjusting the size of patterns P and S, and their elements, on the retina R. Lens 30 may be used to image the optical midpoint of the scanner (halfway between optical elements 24/26 in this figure) onto a mirror 32 to minimize the size of the mirror 32 in an attempt to increase the overall solid angle subtended by a visualization device 34. When mirror 32 is small, it may be placed directly in the visualization path 33 without much disturbance. Mirror 32 may also be placed in the center of a binocular imaging apparatus, such as a Zeiss SL130 slit lamp biomicroscope, without disturbing the visualization. Lens 30 could also be placed one focal length away from the optical midpoint of the scanning optics to produce a telecentric scan, such as is required by certain choices of ophthalmic lens 38. In this case, mirror 32 would need to be large enough to contain the entire scan, and could be made as a high reflector spectrally matched to the output of light source 10 alone. Visualization 34 of the target zone of the eye is accomplished by viewing through mirror 32. A further refinement would be to white balance the transmission of mirror 32, making it photopically neutral, by using a more complicated optical coating that makes the transmitted image appear more natural, rather than, say, pinkish, when using a green notch filter coating on mirror 32. Visualization 34 may be accomplished by directly viewing the retina through mirror 32, or by creating a video image using a camera for display on a remote monitor, or, as indicated by the dashed line, on a graphical user interface 36. An optional ophthalmic lens 38 may be placed directly before the eye to aid in visualization, such as might be done with any ophthalmoscope, slit lamp biomicroscope, fundus camera, SLO, or OCT system. Ophthalmic lens 38 may be a contact or non-contact lens, and may also be used in conjunction with lens 30 to provide for conjugate pupil planes such that the scanning pivots about the patient's iris, thus maximizing the system's retinal scan field.

Figure 11:
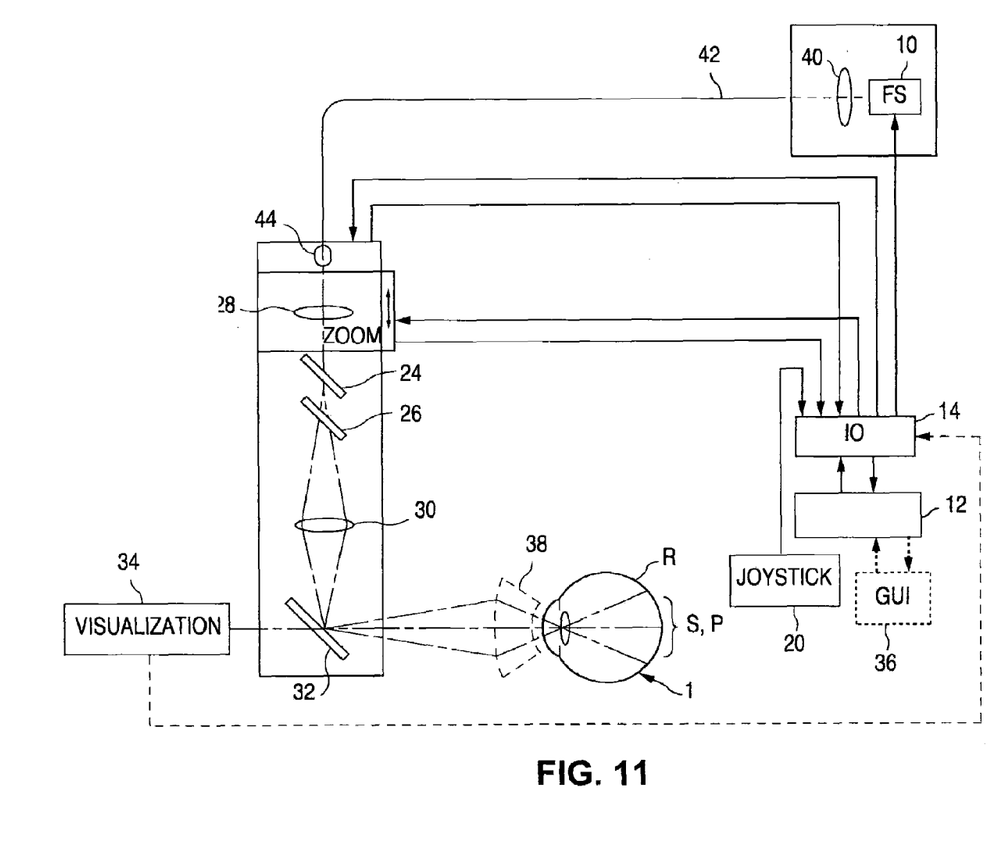
FIG. 11 is a schematic view of a fourth alternate embodiment of the present invention utilizing fiber optic delivery.

FIG. 11 shows a schematic diagram of a fourth alternate embodiment which is similar to that discussed with respect to FIG. 10, but with the addition of fiber optic delivery. In this example, a lens 40 is used to inject the light output 11 into an optical fiber 42. Light exiting optical fiber 42 first encounters lens 44 (for collimation) and then lens 28 (to condition the light prior to its entering the scanner). As before, these lenses may also serve as a zoom system to control the size of patterns P and S, and their elements, on the retina R.

Figure 12:
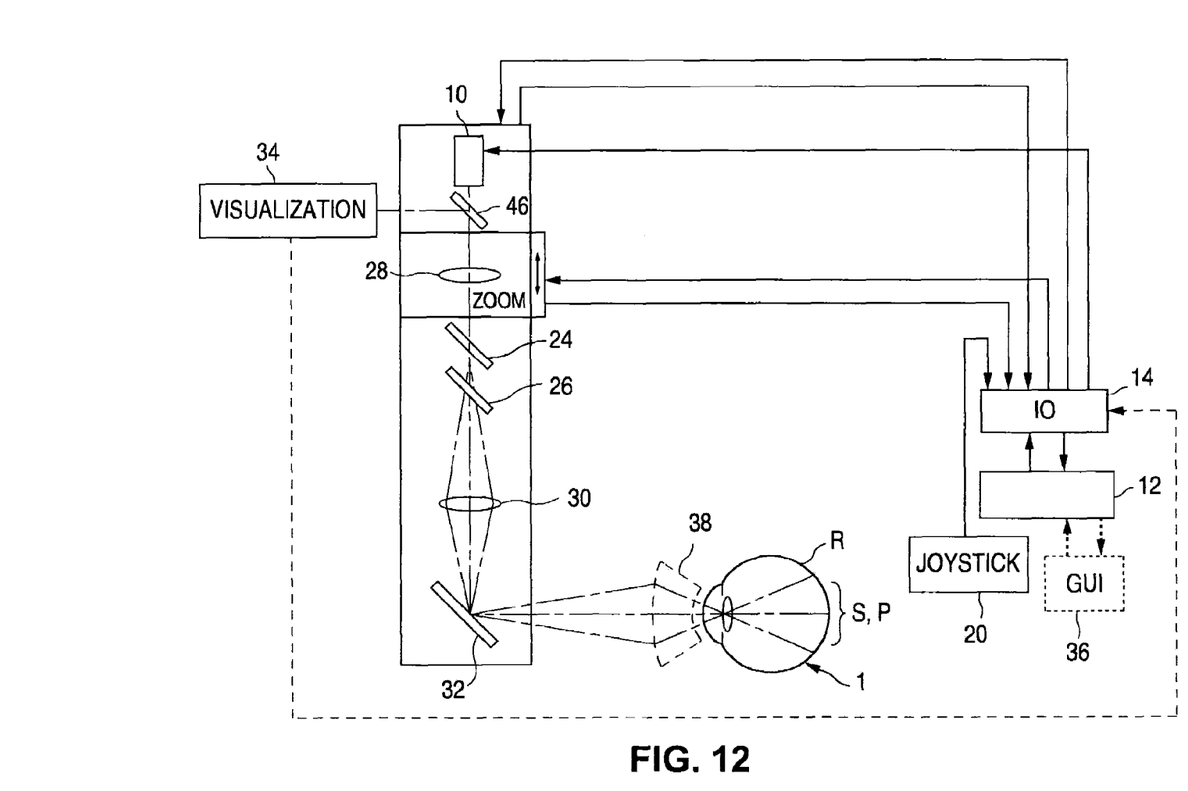
FIG. 12 is a schematic view of a fifth alternate embodiment of the present invention utilizing the scanning mechanism of a scanned ophthalmoscope such an OCT or SLO system where the image is "descanned."

FIG. 12 shows a schematic diagram of a fifth alternate embodiment of the system similar to that shown in FIG. 10, but with the addition of "descanned" visualization, such as might be used in an imaging system like SLO, or OCT. Descanned images are created by gathering the effects of the delivered scanned light reciprocally through the same scanning optics (i.e. optical elements 24/26) that delivered it as, for example, backscatter or fluorescence. Light is delivered forwards through the scanning optics, and the effects of that irradiation are collected backwards through the same scanning optics while they are in nominally the same position, and directed to visualization 34 via a beam splitter 46. The scanning optics may then be moved, and the process repeated. In this way, an image may be built in a point-by-point manner using a minimum of optical elements. In this example, mirror 32 is used to retrieve the descanned light. Of course, this approach is general, and will work with all of the embodiments of the present invention as well.

Figure 13:
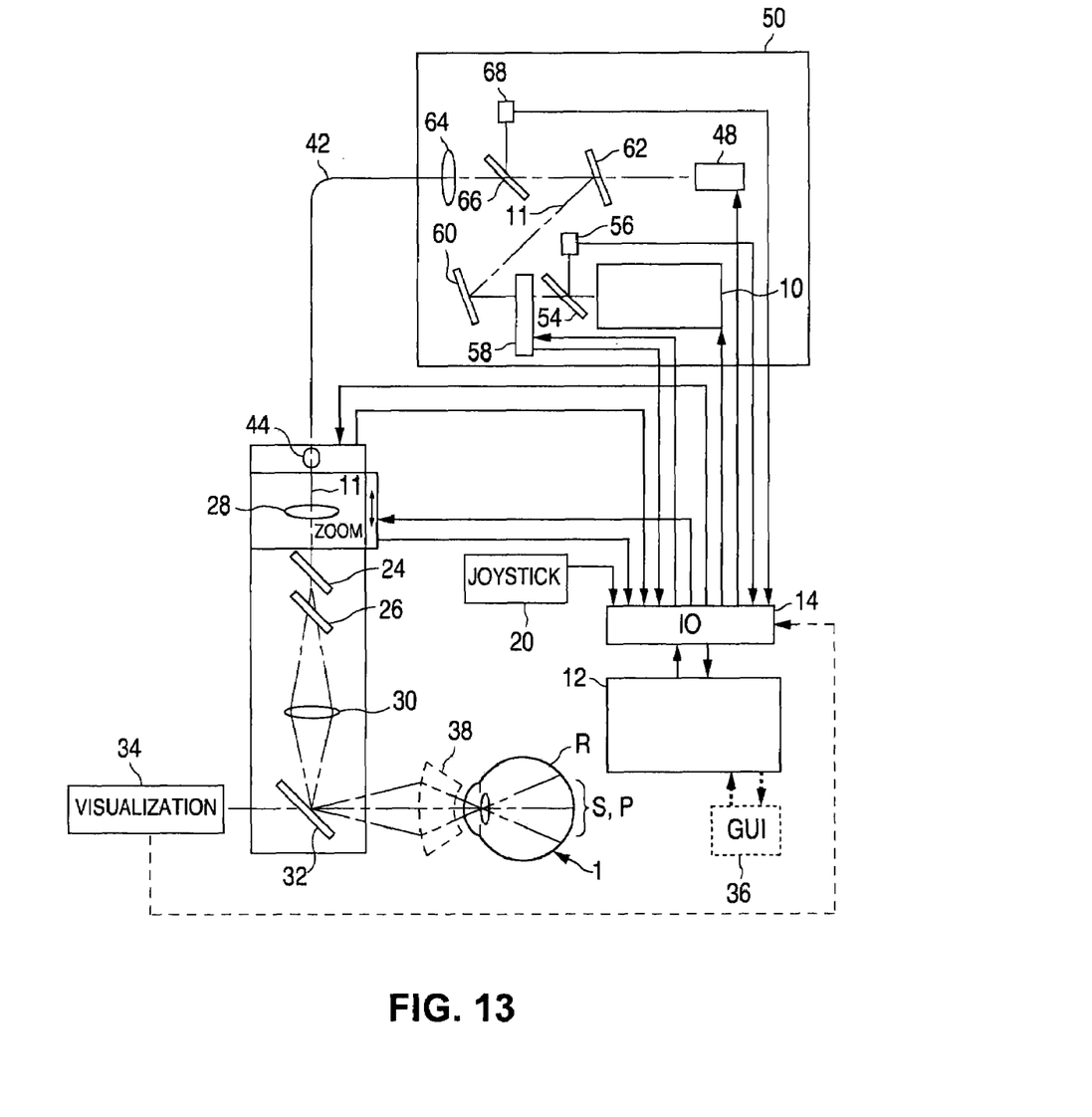
FIG. 13 is a schematic view of a sixth alternate embodiment of the present invention embedded into a host system.

FIG. 13 shows a schematic diagram of a sixth embodiment which is similar to that discussed with respect to FIG. 11, but additionally includes aiming light, beam shuttering, and power measurements, such as may be found in a commercial photo-medical device. In this embodiment, light output from source 10 first encounters mirror 54 which directs a portion of the light to a sensor 56 (e.g. photodiode) which serves to sample and measure the power of the light for safety purposes. Following that, the light then encounters shutter 58, mirror 60, and mirror 62. Shutter 58 fundamentally serves to control the delivery of the light beam 11 (e.g. used to gate the light, in addition to grossly blocking it). Mirror 60 is shown as a turning mirror, where it might also be used in conjunction with mirror 62 to align the light beam 11 into fiber optic 42. Mirror 62 is shown as a combining mirror for combining aiming light from aiming light source 48, and for directing the combined light into fiber optic 42 via lens 64. Aiming light is visible light coincident upon the fixation/procedure light for aiming purposes (to visually indicate the location of beams passing through the scanning optics). Mirror 66 is used to direct some of the light from both light sources 10/48 to sensor 68 (e.g. photodiode) to also sample the light and measure its power (i.e. additionally allowing for a redundant monitor of the state of shutter 58). Fiber optic 42 is not strictly required, but is shown as an example. Free-space delivery of the light may be desirable in certain circumstances, in which case mirrors 60 and 62 may be used to align and or scan the optical output of light source 10 and the aiming light source 48 directly or in conjunction with scanning optics 24/26.

Figure 14:
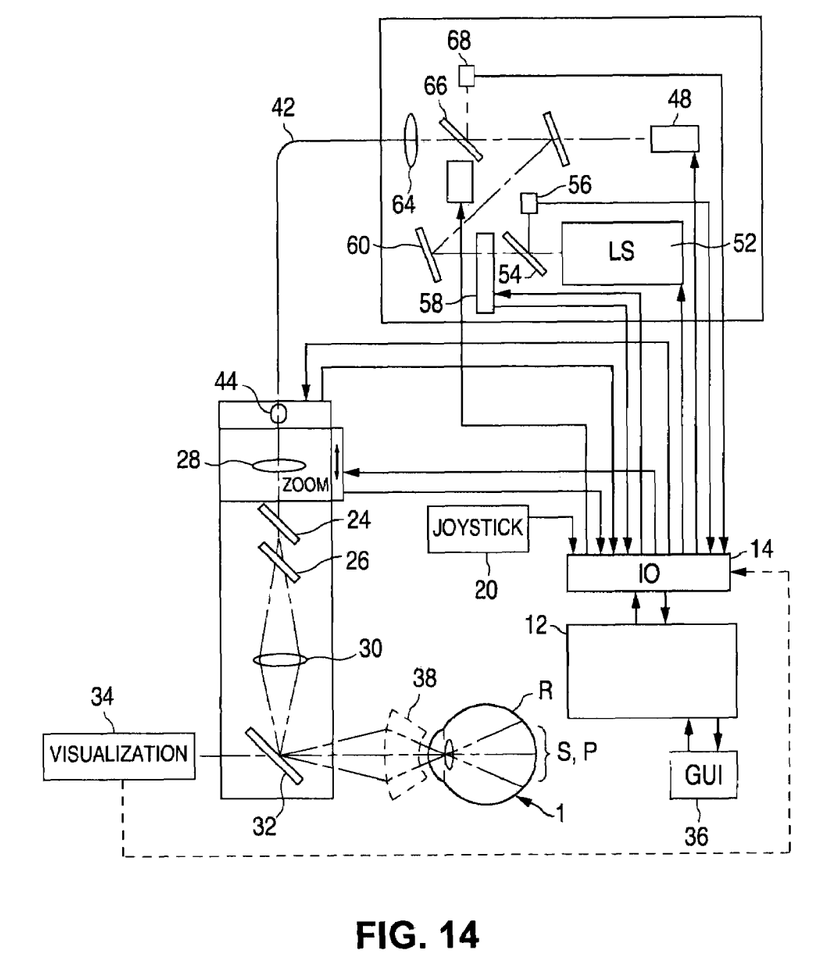
FIG. 14 is a schematic view of a seventh alternate embodiment of the present invention embedded into a host system incorporating separate S pattern, P pattern and aiming light sources.

FIG. 14 shows a schematic diagram of a seventh embodiment of the present invention which is similar to that described above with respect to FIG. 13, but with the addition of a separate light source 52. In this embodiment, light source 10 provides the light for pattern P, and light source 52 provides the light for pattern S. In this embodiment, mirror 66 is a dichroic mirror used to combine the P and S pattern light together. All three lights sources can be controlled by the host system's control electronics 12 via input and output device 14.

Figure 15:
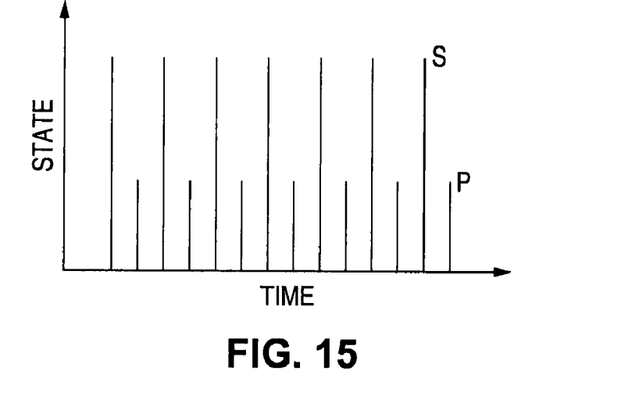
FIG. 15 is a timing diagram illustrating how patterns P and S can be temporally interleaved.
Figure 16:
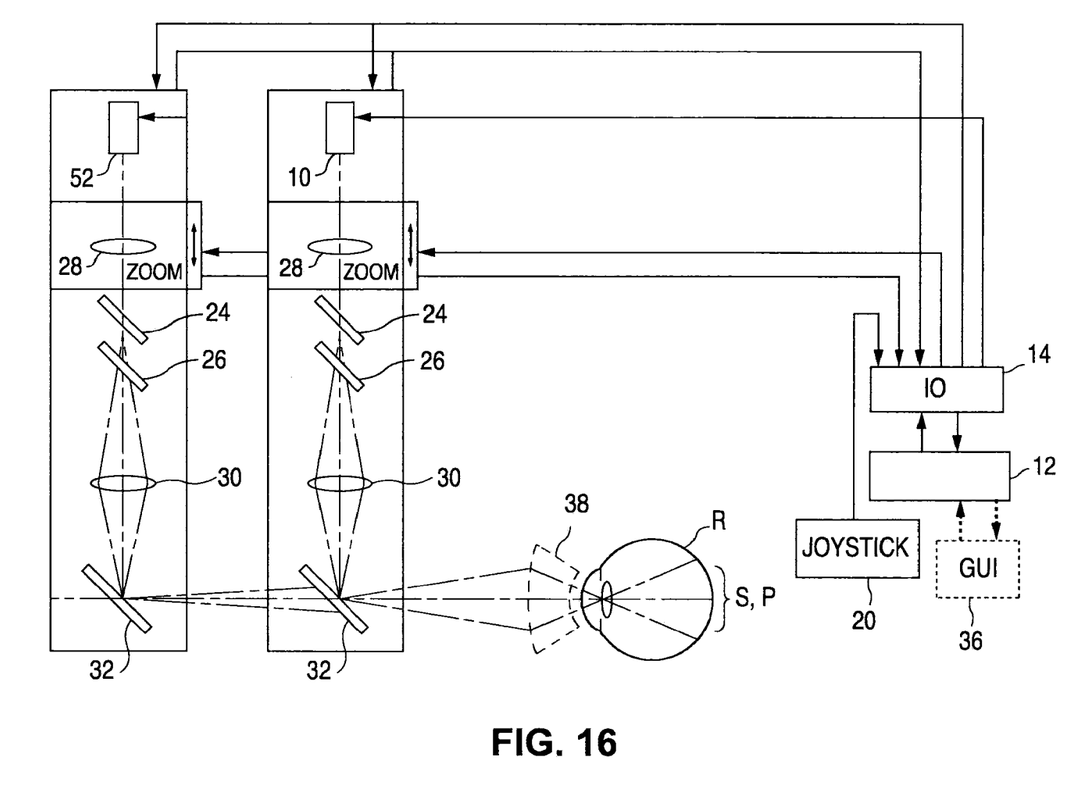
FIG. 16 is a schematic view of an eighth alternate embodiment of the present invention embedded into a host system incorporating separate scanning devices for generating S and P patterns.

FIG. 15 shows a timing diagram of one of many possible schemes for temporally interleaving patterns P and S in any of the above embodiments. The number, permutation, and duration of the individual scan elements may vary to suit the particular clinical need. By interleaving the timing of P and S light patterns, these patterns can be individually and independently imaged onto the eye using the same scanning optical elements, which minimizes the number and complexity of the optical elements used for light delivery. However, temporal interleaving need not be implemented, for example, if the scanning component is divided to provide separate scanning optics for each of the light sources 10 and 52 (as illustrated in FIG. 16). Such a configuration would provide the possibility for delivering patterns P and S to different eyes.

It is to be understood that the present invention is not limited to the embodiment(s) described above and illustrated herein, but encompasses any and all variations falling within the scope of the appended claims. For example, as is apparent from the claims and specification, not all method steps need be performed in the exact order illustrated or claimed, but rather in any order that achieves the fixation and treatment/diagnostic advantages of the present invention.

What is claimed is:

1. An optical scanning system for treating and/or diagnosing a patient's eye, comprising:
    a light source for producing fixation light which is light for attracting and keeping said patient's gaze in a nominally fixed direction and procedure light which is light for treating and/or diagnosing said patient's eye;
    a scanning device for deflecting the fixation light to produce a fixation pattern of the fixation light on the eye, and for deflecting the procedure light to produce a procedure pattern of the procedure light on the eye; and
    a controller for controlling the scanning device such that at least one of the fixation and procedure patterns on the eye is moved relative to the other of the fixation and procedure patterns on the eye.

2. The system of claim 1, wherein the light source comprises:
    a first light producing component for producing the fixation light; and
    a second light producing component separate from the first light producing component for producing the procedure light.

3. The system of claim 2, wherein the fixation light has a wavelength that is different than that of the procedure light.

4. The system of claim 1, further comprising:
    a shutter for intermittently blocking at least one of the fixation light and the procedure light.

5. The system of claim 1, wherein the fixation pattern and procedure pattern are produced on the eye in a temporally interleaved manner.

6. The system of claim 5, wherein the scanning device comprises:
    a movable optical element for deflecting both the fixation light and the procedure light.

7. The system of claim 1, wherein the scanning device comprises:
    a first movable optical element for deflecting the fixation light independently from deflections of the procedure light; and
    a second movable optical element for deflecting the procedure light independently from deflections of the fixation light.

8. The system of claim 1, wherein the scanning device causes the fixation pattern to remain stationary relative to the eye and the procedure pattern to move relative to the eye.

9. The system of claim 1, wherein the scanning device causes the fixation pattern to move relative to the eye and the procedure pattern to remain stationary relative to the eye.

10. The system of claim 1, wherein at least one of the fixation pattern and the procedure pattern includes one or more individual spots.

11. The system of claim 1, wherein at least one of the fixation pattern and the procedure pattern includes a continuously scanned segment.

12. The system of claim 1, wherein:
    the light source produces additional light;
    the scanning device deflects the additional light to produce a system information pattern of the additional light on the eye; and
    the system information pattern indicates status information of the system.

13. The system of claim 1, further comprising:
    a movable focusing optical element for altering a size of at least one of the fixation pattern and the procedure pattern on the eye.

14. The system of claim 1, wherein the light source produces visible aiming light, and wherein the scanning device deflects the aiming light for visually indicating a position of the procedure pattern on the eye.

15. The system of claim 1, wherein the light source comprises:
    a first light producing component for producing the fixation light; and
    a second light producing component separate from the first light producing component for producing the procedure light; and
    a third light producing component separate from the first and second light producing components for producing aiming light, wherein the scanning device deflects the aiming light for visually indicating a position of the procedure pattern on the eye.

16. The system of claim 1, wherein the procedure pattern and the fixation pattern are produced on the eye simultaneously.

17. A method of treating and/or diagnosing a patient's eye, comprising:
    generating fixation light which is light for attracting and keeping said patient's gaze in a nominally fixed direction;
    generating procedure light which is light for treating and/or diagnosing said patient's eye;
    deflecting the fixation light to produce a fixation pattern of the fixation light on the eye;
    deflecting the procedure light to produce a procedure pattern of the procedure light on the eye; and
    moving at least one of the fixation and procedure patterns on the eye relative to the other of the fixation and procedure patterns on the eye.

18. The method of claim 17, wherein the generating of the fixation light is performed using a first light component, and wherein the generating of the procedure light is performed using a second light component that is separate from the first light component.

19. The method of claim 17, wherein the fixation light has a wavelength that is different than that of the procedure light.

20. The method of claim 17, further comprising:
    intermittently blocking at least one of the fixation light and the procedure light.

21. The method of claim 17, wherein the fixation pattern and procedure pattern are produced onto the eye in a temporally interleaved manner.

22. The method of claim 21, wherein the deflectings of the fixation and procedure light include moving an optical element on which both the fixation light and the procedure light are incident.

23. The method of claim 17, wherein:
the deflecting of the fixation light includes moving a first optical element on which the fixation light is incident; and
the deflecting of the procedure light includes moving a second optical element on which the procedure light is incident.

24. The method of claim 17, wherein:
the deflectings of the fixation and procedure light cause the fixation pattern to remain stationary relative to the eye and the procedure pattern to move relative to the eye.

25. The method of claim 17, wherein:
the deflectings of the fixation and procedure light cause the fixation pattern to move relative to the eye and the procedure pattern to remain stationary relative to the eye.

26. The method of claim 17, wherein at least one of the fixation pattern and the procedure pattern includes one or more individual spots.

27. The method of claim 17, wherein at least one of the fixation pattern and the procedure pattern includes a continuously scanned segment.

28. The method of claim 17, further comprising:
generating additional light; and
deflecting the additional light to produce a system information pattern of the additional light on the eye, wherein the system information pattern indicates status information.

29. The method of claim 17, further comprising:
moving a focusing optical element to altering a size of at least one of the fixation pattern and the procedure pattern on the eye.

30. The method of claim 17, further comprising:
generating visible aiming light; and
deflecting the aiming light to produce visible light on the eye indicating a position of the procedure pattern on the eye.

31. The method of claim 17, wherein the procedure pattern and the fixation pattern are produced on the eye simultaneously.

* * * * *